United States Patent
Lin et al.

(10) Patent No.: US 10,396,530 B2
(45) Date of Patent: Aug. 27, 2019

(54) AIR NEGATIVE ION GENERATING APPARATUS REALIZED BY BUMPING AGAINST COLLISION SURFACE BY HIGH-PRESSURE GAS FLOW CARRYING WATER MOLECULES

(71) Applicants: HANGZHOU ESTAI MEDICAL TECHNOLOGY CO., LTD, Hangzhou (CN); TSINGHUA UNIVERSITY, Beijing (CN)

(72) Inventors: Jinming Lin, Beijing (CN); Shaoen Luo, Hangzhou (CN); Yimin Chen, Hangzhou (CN); Zhenghua Dai, Hangzhou (CN); Fengcan Lu, Hangzhou (CN); Liu Hong, Hangzhou (CN); Qunfeng Jiang, Hangzhou (CN); Shunyao Cai, Hangzhou (CN)

(73) Assignees: Hangzhou Estai Medical Technology Co., LTD, Hangzhou (CN); Tsinghua University, Beijing (CN)

( * ) Notice: Subject to any disclaimer, the term of this patent is extended or adjusted under 35 U.S.C. 154(b) by 0 days.

(21) Appl. No.: 16/080,310

(22) PCT Filed: Jan. 14, 2016

(86) PCT No.: PCT/CN2016/070877
§ 371 (c)(1),
(2) Date: Aug. 28, 2018

(87) PCT Pub. No.: WO2017/092159
PCT Pub. Date: Jun. 8, 2017

(65) Prior Publication Data
US 2019/0074666 A1    Mar. 7, 2019

(30) Foreign Application Priority Data

Dec. 3, 2015 (CN) .......................... 2015 1 0880859

(51) Int. Cl.
*H01T 23/00* (2006.01)
*A61L 9/22* (2006.01)
*F24F 3/16* (2006.01)

(52) U.S. Cl.
CPC ................ *H01T 23/00* (2013.01); *A61L 9/22* (2013.01); *F24F 3/16* (2013.01); *F24F 2003/1682* (2013.01)

(58) Field of Classification Search
CPC .... H01T 23/00; A61L 9/22; F24F 3/16; F24F 2003/1682
See application file for complete search history.

(56) References Cited

U.S. PATENT DOCUMENTS

| | | |
|---|---|---|
| 5,591,334 A | 1/1997 | Shimizu et al. |
| 2006/0102001 A1* | 5/2006 | Shin ..................... B01D 47/085 96/283 |

FOREIGN PATENT DOCUMENTS

| | | | |
|---|---|---|---|
| CN | 1053552 A | * | 8/1991 |
| CN | 1053552 A | | 8/1991 |

(Continued)

*Primary Examiner* — David E Smith
(74) *Attorney, Agent, or Firm* — Schwegman Lundberg & Woessner, P.A.

(57) ABSTRACT

An air negative ion generating apparatus realized by bumping against a collision surface by a high-pressure gas flow carrying water molecules includes a liquid container and a cover body snapped onto a top opening end of the liquid container, and the cover body is provided with a high-pressure gas inlet pipe; a core assembly is provided inside the cover body, and the core assembly (4) includes a liquid flow chamber, a collision component and a liquid flow inlet; and a lower port of the high-pressure gas inlet pipe faces the collision component, the liquid flow inlet is located between the lower port of the high-pressure gas inlet pipe and the collision component, the liquid flow inlet is communicated with the liquid chamber, and a lower port of the liquid flow (Continued)

chamber is fixedly connected with a liquid conduit extending downwards.

20 Claims, 4 Drawing Sheets

(56) References Cited

FOREIGN PATENT DOCUMENTS

| | | | |
|---|---|---|---|
| CN | 2141711 Y | | 9/1993 |
| CN | 2801169 Y | | 8/2006 |
| CN | 205159793 U | | 4/2016 |
| JP | 10141717 A | * | 5/1998 |
| JP | 10160211 A | | 6/1998 |
| JP | 2000161727 A | | 6/2000 |
| KR | 20040105424 A | * | 12/2004 |

* cited by examiner

AIR NEGATIVE ION GENERATING APPARATUS REALIZED BY BUMPING AGAINST COLLISION SURFACE BY HIGH-PRESSURE GAS FLOW CARRYING WATER MOLECULES

CROSS REFERENCE TO RELATED APPLICATIONS

This application is a national phase entry of PCT/CN2016/070877 filed Jan. 14, 2016, which claims priority to CN201510880859.0 filed Dec. 3, 2015, both of which are incorporated herein by reference.

BACKGROUND OF THE INVENTION

Field of the Invention

This invention relates to an air negative ion generating apparatus realized by bumping against a collision surface by a high-pressure gas flow carrying water molecules, which belongs to a medical and health field.

Description of the Related Art

Negative oxygen ions and associated negative air ions, which are referred to as "air vitamins", have received a great deal of attention in recent years. A concentration of negative ions in a certain area has become one of the important indicators evaluating air quality and livability of the area. In general, substances are made of molecules, molecules are made of atoms, and the atoms are made of negatively charged electrons and positively charged nuclei. Under external force, the two are separated, the substance is charged, and the substance that get electrons shows negative charge. Due to an inherent stability of neutral molecules, they are not easy to obtain electrons. Under external action such as radiation, ultraviolet light, lightning, physical shock, or corona discharge, some electrons at an outer layer will escape from the nucleus to form free electrons and be further captured by neutral molecules to form negative ions. In addition, some of the electrons are not trapped, but attack other molecules to ionize the molecules and give electrons to the molecules. This process is repeated to form a chain reaction process of constantly collision and capture, thereby continuing to generate a large number of negative ions. Every time people walk in natural environments such as a forest, a waterfall, and a grassland, they always feel comfortable and refreshed, because these places are rich in negative ions that are beneficial to human health. In contrast, the concentration of negative ions in the natural environment is higher than 100,000/cm$^3$, while buildings and offices in cities have only a few dozen/cm$^3$ or even zero. In various environments, negative ions continue to be generated and disappear, and eventually the concentration is maintained in a stable range. Similarly, average lifetime of negative ions is generally tens of seconds to several minutes. In natural environments such as a seashore, the forest, the grassland and the waterfall, their lifetime is a little longer and about 20 minutes. In cities, their lifetime is extremely short, only a few seconds. Studies show that negative ions not only can remove dust and reduce dust in the environment, but also have excellent health care effects on the human body, especially in the aspects of increasing blood oxygen content, lowering blood pressure, refreshing, helping digestion and promoting metabolism.

At present, there are many kinds of negative ion generating apparatus on the market, which are mainly divided into several categories: a vehicle-type, a home-type, and a office-type, and their qualities are also uneven. A main production way is to ionize air by corona discharge and generate free electrons which further combine with neutral molecules to form negative ions. This technology has advantages of mature technology, low cost, large content of negative ions and simple device. However, there are also disadvantages such as high content of by-products such as ozone and nitrogen oxides and obvious electrostatic effects, which limits widespread popularization and application of negative ion technology in the corona discharge.

In recent years, the air quality problem has gradually become a major killer of the environment and the human body. Preventing air pollution and restoring a clear blue sky have become a top priority. At present, some air purifiers on the market try to simply use a plurality of filters to filter out small particles and purify the air. However, such device only filters out solid particles from the surface and do not fundamentally improve the air quality. In contrast, studies have shown that negative ions can not only effectively degrade small particles in the air, prevent a hazard of PM 2.5, but also continue to release negative ions into the treated air, which integrates dual effects of degradation and release, thus truly improve the air quality.

Therefore, there is an urgent need for a novel negative ion generating apparatus with high negative ion content and safe without by-products, which can ensure a large amount of negative ions being supplied with high efficiency and low cost, without the generation of ozone and nitrogen oxides, and without electrostatic effect, and so as to truly utilize advantages of negative ions and enjoy the purification and health effects of negative ions.

BRIEF SUMMARY OF THE INVENTION

To solve the above-mentioned problems, the objective of this invention is to provide an air negative ion generating apparatus realized by bumping against a collision surface by a high-pressure gas flow carrying water molecules, which can generate a large number of negative ions and be safe without byproducts.

To achieve the above-mentioned objective, this invention adopts the following technical solution: an air negative ion generating apparatus realized by bumping against a collision surface by a high-pressure gas flow carrying water molecules includes a liquid container and a cover body snapped onto a top opening end of the liquid container, and the cover body is provided with a high-pressure gas inlet pipe; a core assembly is provided in the cover body, and the core assembly comprises a liquid flow chamber, a collision component and a liquid flow inlet; and a lower port of the high-pressure gas inlet pipe faces the collision component, the liquid flow inlet is located between the lower port of the high-pressure gas inlet pipe and the collision component, the liquid flow inlet is communicated with the liquid chamber, and a lower port of the liquid flow chamber is fixedly connected with a liquid conduit extending downwards.

A water gas collision cabin is provided in the cover body, the core assembly is located in the water gas collision cabin, and the water gas collision cabin is communicated with an interior space of the cover body.

The high-pressure gas inlet pipe is fixedly connected with the cover body and a lower end extends into the water gas collision cabin.

A top of the cover body is provided with a negative pressure air inlet communicated with the water gas collision cabin; and the cover body is provided with an air outlet, and the air outlet is communicated with the interior space of the cover body located outside the water gas collision cabin.

The negative pressure air inlet of the cover body is provided with a flow regulating valve for changing air inlet flow.

An area of the lower port of the high-pressure gas inlet pipe is 1/10 of an area of an upper port.

The liquid container is made of glass or plastic.

The core assembly is made of a hard material.

This invention has the following advantages due to the adoption of the above-mentioned technical solution: 1. In this invention, by disposing the high-pressure gas inlet pipe at the top of the cover body, disposing the collision component at the lower port of the high-pressure gas inlet pipe, disposing the liquid flow inlet between the collision component and the lower port of the high-pressure gas inlet pipe, communicating the liquid flow inlet with the liquid flow chamber, and connecting the liquid flow chamber with the liquid conduit, when the high-pressure gas passes through the high-pressure gas inlet pipe, the high-speed gas flow rushes towards the collision component, and the high-speed gas flow generates a negative pressure at the liquid flow inlet when passing through the liquid flow inlet. Water is sucked up through the liquid conduit and mixed with the high-speed gas flow, thereby a gas-liquid mixture of the high-speed gas carrying liquid molecules is formed; and when the gas-liquid mixture bumps against the collision component, negative ions will be generated. 2. By disposing the water gas collision cabin in the cover body, disposing the core assembly in the water gas collision cabin, and providing the negative pressure air inlet communicated with the water gas collision cabin at the top of the cover body, when the high-pressure air passes through the high-pressure gas inlet pipe and enters into the water gas collision cabin to form the high-speed gas flow, the water gas collision cabin will generate a wind pipe effect which forms a negative pressure, facilitate the external air to pass through the negative pressure air inlet to enter into the water gas collision cabin and promote moving of hydrated negative ions from the air outlet of the cover body to an external air environment. 3. In this invention, as the area of the lower port of the high-pressure gas inlet pipe is 1/10 of the area of the upper port, when the high-speed gas passes through the high-pressure gas inlet pipe, the speed of the air flow can be increased by 8-10 times. 4. The invention avoids the generation of harmful by-products such as ozone, nitrogen oxides and the like while ensuring the production and release of a large number of negative ions, and this invention does not require any additional power source, does not generate electrostatic effects, has low manufacturing cost, has environmental materials and is environmentally friendly.

BRIEF DESCRIPTION OF THE DRAWINGS

The present invention is described in detail below with reference to the accompanying drawings. However, it should be understood that the drawings are provided only for a better understanding of this invention, and they should not be construed as a limitation of this invention.

DETAILED DESCRIPTION OF THE INVENTION

Figure 1:
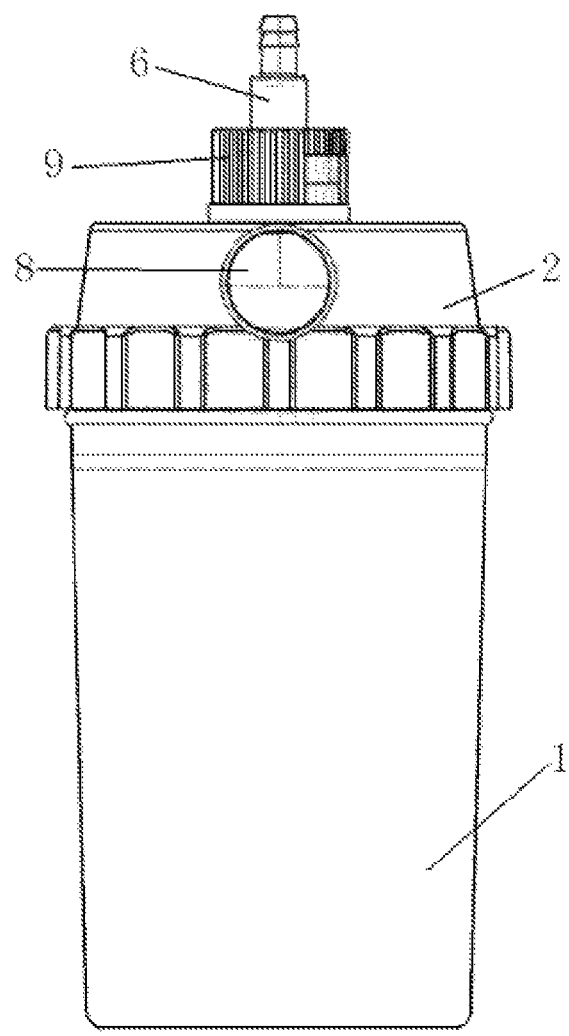
FIG. 1 is a schematic diagram of an external structure of this invention.
Figure 2:
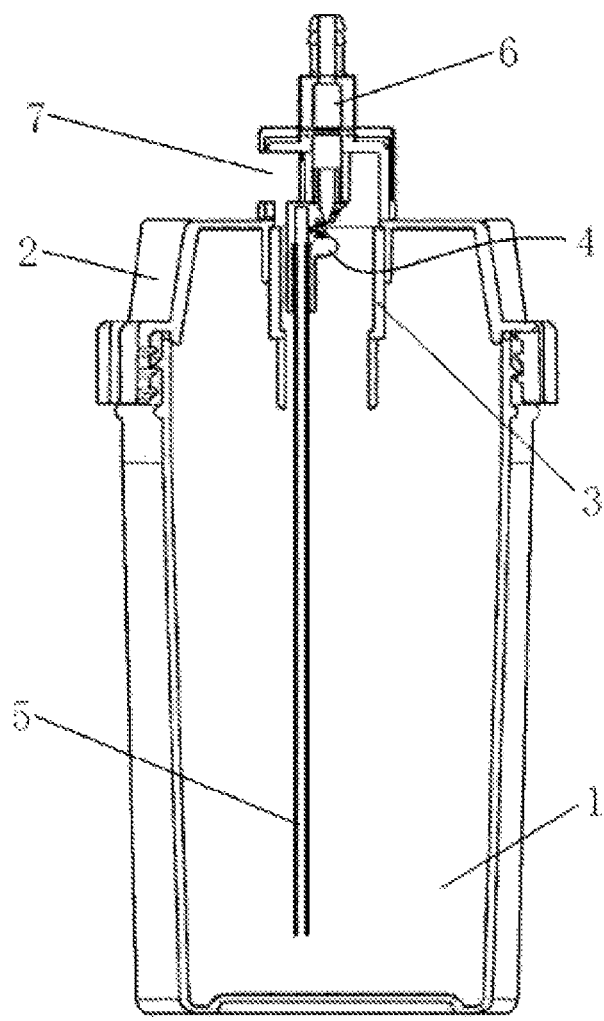
FIG. 2 is a schematic diagram of an internal structure of this invention.
Figure 3:
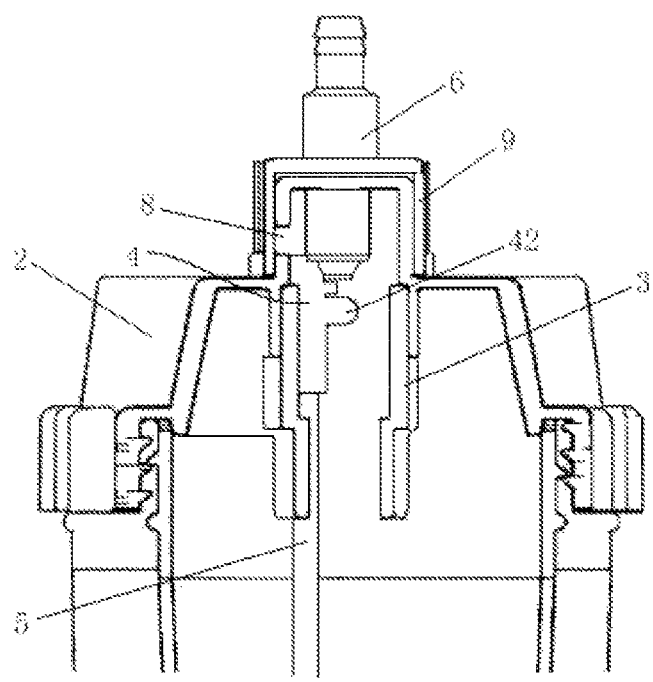
FIG. 3 is a schematic diagram of an internal structure of a cover body of this invention.
Figure 4:
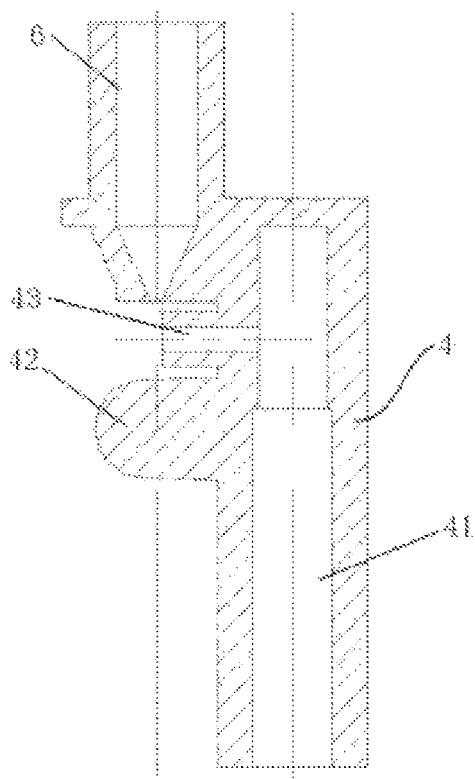
FIG. 4 is a structural schematic diagram of a core assembly of this invention.
Figure 5:
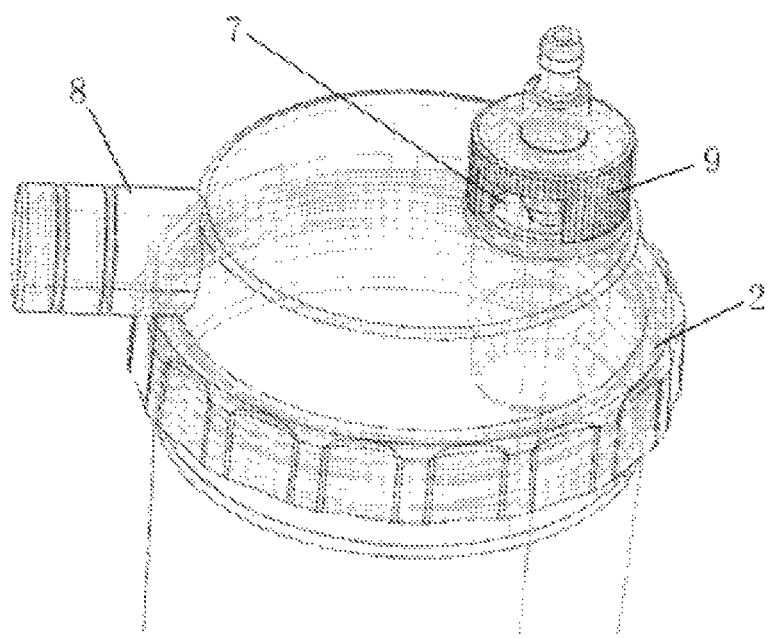
FIG. 5 is a schematic diagram of a three-dimensional structure of the cover body of this invention.

As shown in FIG. 1-FIG. 3, this invention provides an air negative ion generating apparatus realized by bumping against a collision surface by a high-pressure gas flow carrying water molecules which includes a liquid container 1 and a cover body 2 snapped onto a top opening end of the liquid container 1 in a sealing way. A water gas collision cabin 3 is disposed in the cover body 2, a lower end of the water gas collision cabin 3 is open, and the water gas collision cabin 3 is communicated with the liquid container 1 and an interior space of the cover body 2 located outside the water gas collision cabin 3. A core assembly 4 is disposed inside the water gas collision cabin 3. As shown in FIG. 4, the core assembly 4 includes a liquid flow chamber 41, a collision component 42 and a liquid flow inlet 43, wherein the collision component 42 is disposed at an outer wall of the liquid flow chamber 41, the liquid flow inlet 43 is located above the collision component 42 and is communicated with the liquid flow chamber 41, a liquid conduit 5 is fixedly connected with a lower port of the liquid flow chamber 41, and the liquid conduit 5 is vertically arranged and extends near the bottom of the liquid container 1. A high-pressure gas inlet pipe 6 is disposed at the cover body 2, the high-pressure gas inlet pipe 6 extends into the water gas collision cabin 3 and a lower port faces the collision component 42. The liquid flow inlet 43 is located between a lower port of the high-pressure gas inlet pipe 6 and the collision component 42. A negative pressure air inlet 7 (as shown in FIG. 5) is disposed at the top of the cover body 2 communicated with the water gas collision cabin 3 which is used to send air into the water gas collision cabin 3. The cover body 2 is provided with an air outlet 8, and the air outlet 8 is communicated with the interior space of the cover body 2 located outside the water gas collision cabin 3.

In a preferred embodiment, a flow regulating valve 9 is disposed at the negative pressure air inlet 7 of the cover body 2, and the size of the negative pressure air inlet 7 can be changed by rotating the flow regulating valve 9, such the air flow entering the cover body 2 is regulated, thereby achieving the purpose of adjusting the air flow sent through the air outlet 8.

In a preferred embodiment, the area of the lower port of the high-pressure gas inlet pipe 6 is 1/10 of the area of the upper port, such that when the high-speed gas passes through the high-pressure gas inlet pipe 6, the speed of the air flow can be increased by 8-10 times.

In a preferred embodiment, the liquid container 1 is made of glass, plastic and so on; and the core assembly 4 is made of a hard material such as metal and polymer, which can enhance water and gas bumping resistance.

A working process of this invention is as follows: the high-pressure gas inlet pipe 6 of this invention is connected with an air source of high-pressure air, and when the air source of the high-pressure air is turned on, the high-pressure air rushes out from the lower port of the high-pressure gas inlet pipe 6, and generated high-speed air flow rushes toward the collision component 42. As the high-speed air generates a negative pressure at the liquid flow inlet 43 when passing through the liquid flow inlet 43, water is sucked up to the liquid flow inlet 43 through the liquid conduit 5 and mixed with the high-speed air flow, thereby a gas-liquid mixture of the high-speed gas carrying liquid molecules is formed; and when the gas-liquid mixture bumps against the collision component 43, negative ions are generated. As the high-speed air flow causes the negative pressure at the water gas collision cabin 3, external air enters the water gas collision cabin 3 through the negative pressure air inlet 7, pushing the hydrated negative ions into the interior space of the cover body 2 located outside the water gas collision cabin 3, and further the hydrated negative ions being moved from the air outlet 8 to the external environment, so as to generate a mist-like air flow carrying a large number of air negative ions. Relevant reaction equations of this invention are summarized as follows:

$$H_2O \rightarrow H_2O^+ + e^-$$

$$H_2O + e \rightarrow H^- + OH$$

$$H^- + H_2O \rightarrow OH^- + H_2$$

$$OH^- + nH_2O \rightarrow OH^-(H_2O)_n$$

$$e + O_2 \rightarrow O_2^-$$

$$e + O_2 \rightarrow O^- + O$$

$$O_2^- + nH_2O \rightarrow O_2^-(H_2O)_n$$

$$O^- + nH_2O \rightarrow O^-(H_2O)_n$$

$$O^- + NO_2 \rightarrow NO_3^-$$

$$O_2^- + NO \rightarrow NO_3^-$$

$$OH^- + CO_2 \rightarrow HCO_3^-$$

$$HCO_3^- + nH_2O \rightarrow HCO_3^-(H_2O)_n$$

$$OH^- + O_3 \rightarrow HO_2^- + O_2$$

$$HO_2^- + CO_2 \rightarrow HCO_4^-$$

$$HCO_4^- + nH_2O \rightarrow HCO_4^-(H_2O)_n$$

This invention has been experimentally tested. Pure water is used as the liquid, 5 kg of the air is used as the gas source of the high-pressure gas, and a detection device is used at a distance of 60 cm from the air outlet 7 for detection. The result shows that the highest negative ion concentration can reach 916 thousand/$cm^3$, the average negative ion concentration reach 786 thousand/$cm^3$, and ozone and electrostatic phenomenon are not detected. This invention can produce negative ions at different concentrations and compositions by changing the composition of the gas or the liquid.

The above embodiments are only used to further specifically describe the objects, technical solutions, and beneficial effects of the present invention and are not intended to limit the present invention. Any modifications, equivalents, and improvements made within the spirit and principles of the present invention should be included in the protection scope of the present invention.

What is claimed is:

1. An air negative ion generating apparatus realized by bumping against a collision surface by a high-pressure gas flow carrying water molecules comprising: a liquid container and a cover body snapped onto a top opening end of the liquid container, wherein the cover body is provided with a high-pressure gas inlet pipe; a core assembly is provided inside the cover body, and the core assembly comprises a liquid flow chamber, a collision component and a liquid flow inlet; and a lower port of the high-pressure gas inlet pipe faces the collision component, the liquid flow inlet is located between the lower port of the high-pressure gas inlet pipe and the collision component, the liquid flow inlet is communicated with the liquid chamber, and a lower port of the liquid flow chamber is fixedly connected with a liquid conduit extending downwards.

2. The air negative ion generating apparatus realized by bumping against the collision surface by the high-pressure gas flow carrying water molecules according to claim 1, wherein a water gas collision cabin is provided inside the cover body, the core assembly is located inside the water gas collision cabin, and the water gas collision cabin is communicated with an interior space of the cover body.

3. The air negative ion generating apparatus realized by bumping against the collision surface by the high-pressure gas flow carrying water molecules according to claim 2, wherein the high-pressure gas inlet pipe is fixedly connected with the cover body and a lower end extends into the water gas collision cabin.

4. The air negative ion generating apparatus realized by bumping against the collision surface by the high-pressure gas flow carrying water molecules according to claim 2, wherein a top of the cover body is provided with a negative pressure air inlet communicated with the water gas collision cabin; and the cover body is provided with an air outlet, and the air outlet is communicated with the interior space of the cover body located outside the water gas collision cabin.

5. The air negative ion generating apparatus realized by bumping against the collision surface by the high-pressure gas flow carrying water molecules according to claim 4, wherein the negative pressure air inlet of the cover body is provided with a flow regulating valve for changing air inlet flow.

6. The air negative ion generating apparatus realized by bumping against the collision surface by the high-pressure gas flow carrying water molecules according to claim 1, wherein an area of the lower port of the high-pressure gas inlet pipe is 1/10 of an area of an upper port.

7. The air negative ion generating apparatus realized by bumping against the collision surface by the high-pressure gas flow carrying water molecules according to claim 1, wherein the liquid container is made of glass or plastic.

8. The air negative ion generating apparatus realized by bumping against the collision surface by the high-pressure gas flow carrying water molecules according to claim 1, wherein the core assembly is made of a hard material.

9. The air negative ion generating apparatus realized by bumping against the collision surface by the high-pressure gas flow carrying water molecules according to claim 2, wherein an area of the lower port of the high-pressure gas inlet pipe is 1/10 of an area of an upper port.

10. The air negative ion generating apparatus realized by bumping against the collision surface by the high-pressure gas flow carrying water molecules according to claim 3, wherein an area of the lower port of the high-pressure gas inlet pipe is 1/10 of an area of an upper port.

11. The air negative ion generating apparatus realized by bumping against the collision surface by the high-pressure gas flow carrying water molecules according to claim 4, wherein an area of the lower port of the high-pressure gas inlet pipe is 1/10 of an area of an upper port.

12. The air negative ion generating apparatus realized by bumping against the collision surface by the high-pressure gas flow carrying water molecules according to claim 5, wherein an area of the lower port of the high-pressure gas inlet pipe is ⅒ of an area of an upper port.

13. The air negative ion generating apparatus realized by bumping against the collision surface by the high-pressure gas flow carrying water molecules according to claim 2, wherein the liquid container is made of glass or plastic.

14. The air negative ion generating apparatus realized by bumping against the collision surface by the high-pressure gas flow carrying water molecules according to claim 3, wherein the liquid container is made of glass or plastic.

15. The air negative ion generating apparatus realized by bumping against the collision surface by the high-pressure gas flow carrying water molecules according to claim 4, wherein the liquid container is made of glass or plastic.

16. The air negative ion generating apparatus realized by bumping against the collision surface by the high-pressure gas flow carrying water molecules according to claim 5, wherein the liquid container is made of glass or plastic.

17. The air negative ion generating apparatus realized by bumping against the collision surface by the high-pressure gas flow carrying water molecules according to claim 2, wherein the core assembly is made of a hard material.

18. The air negative ion generating apparatus realized by bumping against the collision surface by the high-pressure gas flow carrying water molecules according to claim 3, wherein the core assembly is made of a hard material.

19. The air negative ion generating apparatus realized by bumping against the collision surface by the high-pressure gas flow carrying water molecules according to claim 4, wherein the core assembly is made of a hard material.

20. The air negative ion generating apparatus realized by bumping against the collision surface by the high-pressure gas flow carrying water molecules according to claim 5, wherein the core assembly is made of a hard material.

* * * * *